US008914132B2

(12) United States Patent
Jarl et al.

(10) Patent No.: US 8,914,132 B2
(45) Date of Patent: *Dec. 16, 2014

(54) METHOD FOR MANUFACTURING A MEDICAL IMPLANTABLE LEAD

(71) Applicant: St. Jude Medical AB, Jarfalla (SE)

(72) Inventors: Per Jarl, Jarfalla (SE); Rolf Hill, Jarfalla (SE)

(73) Assignee: St. Jude Medical AB, Jarfalla (SE)

( * ) Notice: Subject to any disclaimer, the term of this patent is extended or adjusted under 35 U.S.C. 154(b) by 0 days.

This patent is subject to a terminal disclaimer.

(21) Appl. No.: 14/053,508

(22) Filed: Oct. 14, 2013

(65) Prior Publication Data
US 2014/0041220 A1 Feb. 13, 2014

Related U.S. Application Data

(62) Division of application No. 12/810,613, filed as application No. PCT/SE2007/001123 on Dec. 18, 2007, now Pat. No. 8,594,810.

(51) Int. Cl.
A61N 1/05 (2006.01)
(52) U.S. Cl.
CPC ..................................... A61N 1/056 (2013.01)
USPC .......................................................... 607/127
(58) Field of Classification Search
USPC .......................................................... 607/127
See application file for complete search history.

(56) References Cited

U.S. PATENT DOCUMENTS

| 4,922,607 | A | 5/1990 | Doan et al. |
| 5,466,254 | A | 11/1995 | Helland |
| 5,489,225 | A | 2/1996 | Julian |
| 5,741,321 | A | 4/1998 | Brennen |
| 5,837,006 | A | 11/1998 | Ocel et al. |
| 6,428,336 | B1 | 8/2002 | Akerfeldt |
| 6,755,694 | B2 | 6/2004 | Ries et al. |
| 6,799,991 | B2 * | 10/2004 | Williams et al. ............... 439/482 |
| 7,241,180 | B1 * | 7/2007 | Rentas Torres ............... 439/668 |
| 7,424,180 | B2 | 9/2008 | Park et al. |
| 2008/0288014 | A1 | 11/2008 | Nideborn Warna et al. |

OTHER PUBLICATIONS

Restriction Requirement, mailed Aug. 6, 2012—U.S. Appl. No. 12/810,613.
NonFinal Office Action, mailed Aug. 27, 2012—U.S. Appl. No. 12/810,613.
Final Office Action, mailed Jan. 29, 2013—U.S. Appl. No. 12/810,613.
Advisory Action, mailed May 15, 2013—U.S. Appl. No. 12/810,613.
Notice of Allowance, mailed Sep. 11, 2013—U.S. Appl. No. 12/810,613.

* cited by examiner

Primary Examiner — Eric D. Bertram

(57) ABSTRACT

A medical implantable lead has a header in a distal end, a fixation arrangement and an electrode arranged in the header. The lead also has a connector in a proximal end that includes a connector pin and is adapted to be connected to a monitoring and/or controlling device, and an inner coil, which extends inside an outer casing of the lead and is adapted to transmit electrical signals between the monitoring and/or controlling device and the electrode. The inner coil is attached to the connector pin. The inner coil extends through a bore inside the connector pin and is attached to the connector pin in its proximal end. A method for manufacturing such a lead is also provided.

5 Claims, 4 Drawing Sheets

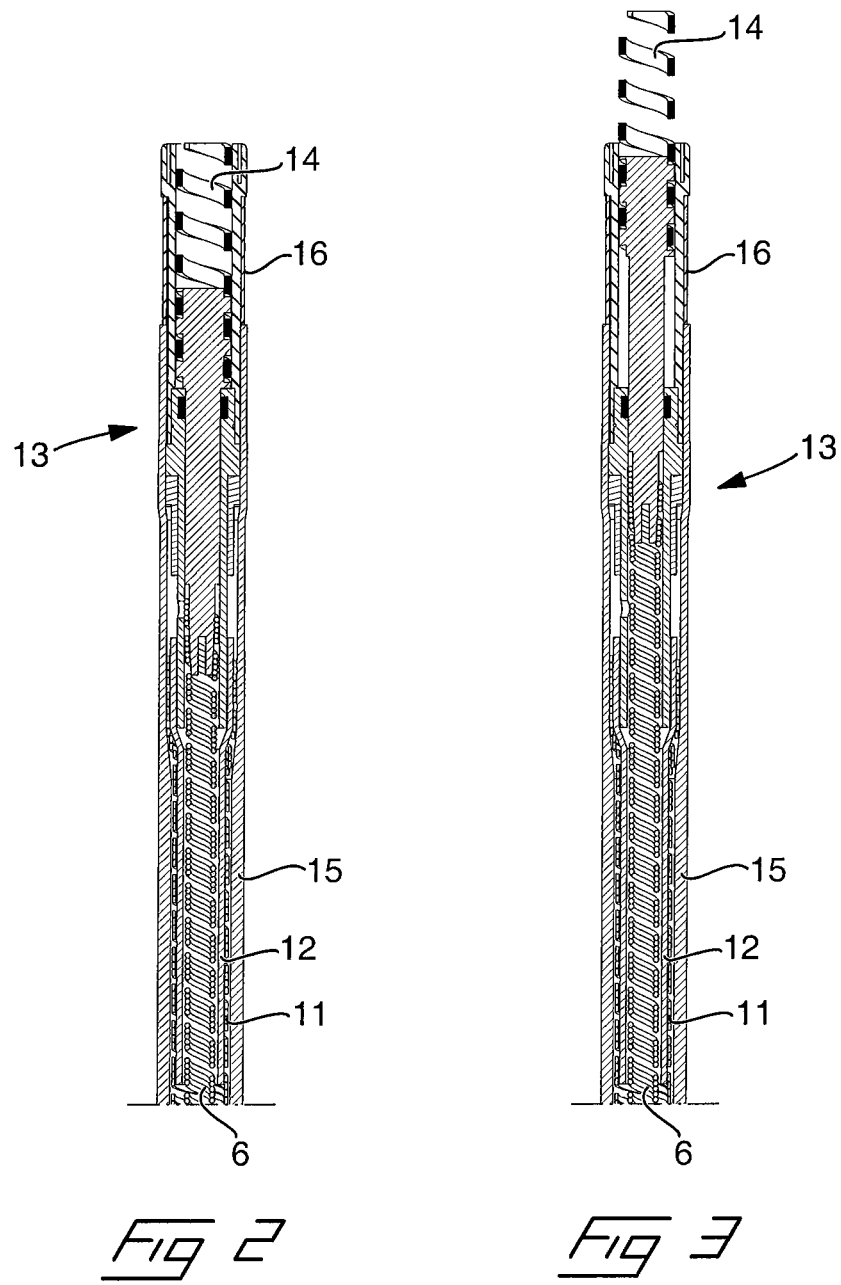

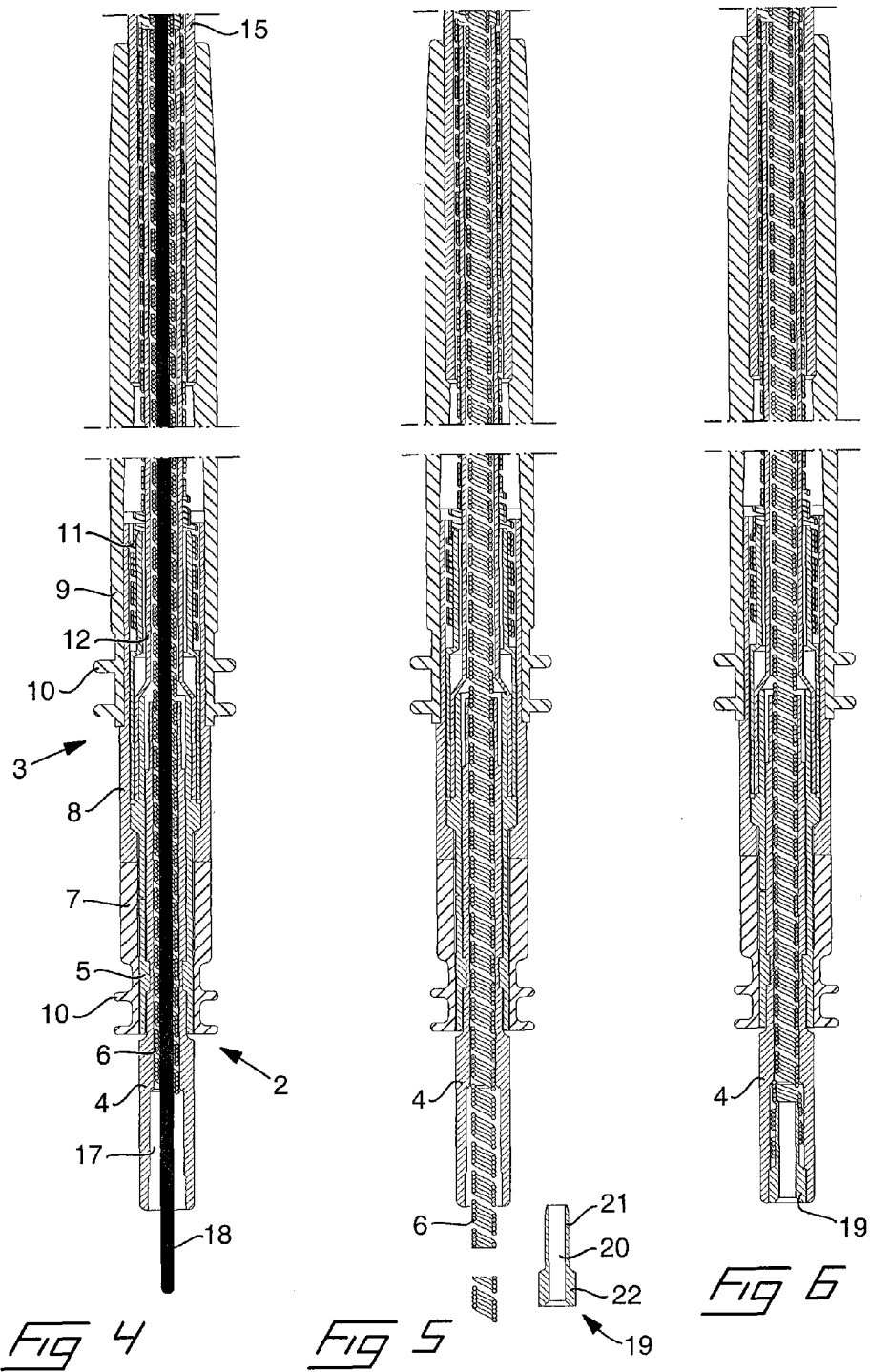

METHOD FOR MANUFACTURING A MEDICAL IMPLANTABLE LEAD

CROSS REFERENCE TO RELATED APPLICATIONS

This application is a division of U.S. patent application Ser. No. 12/810,613, filed Jun. 25, 2010, now U.S. Pat. No. 8,594,810, and which claims priority from Int'l Application No. PCT/SE2007/001123, filed Dec. 18, 2007.

BACKGROUND OF THE INVENTION

1. Field of the Invention

The invention relates to a medical implantable lead of the type adapted to be inserted into a human or animal body and attached to an organ inside the body for monitoring and/or controlling the function of the organ, and having a header in a distal end, a fixation means and an electrode arranged in the header, wherein the fixation means attaches the distal end of the lead to the organ and the electrode is arranged to transmit or receive electrical signals to or from the organ, a connector in a proximal end that includes a connector pin and is adapted to be connected to a monitoring and/or controlling device, and an inner coil, which extends inside an outer casing of the lead and is adapted to transmit electrical signals between the monitoring and/or controlling device and the electrode, wherein the inner coil is attached to the connector pin.

The invention also relates to method for manufacturing of a medical implantable lead of the above type.

2. Description of the Prior Art

Medical implantable leads of the above type are commonly used for example for monitoring and/or controlling the function of a human or animal heart. In such a case a proximal end of the lead is connected to a monitoring and/or controlling device such as a pacemaker or a cardiac defibrillator, whereas a distal end of the lead is inserted into the body and attached to the heart by means of some kind of fixation means. The distal end of the lead comprises at least one electrode, which is in electrical contact with the proximal end by means of an inner coil of helically formed metal wires inside the lead. The fixation means can be of a type having projections, such as fins or tines, which will engage in the trabecular network inside the heart. The fixation means can also be a penetration member, such as a barbed needle or as a helix which is screwed into the tissue of the heart, either as a helix which is unrotatable in relation to the lead, in which case the entire lead is rotated when attaching the helix, or a rotatable helix which can be rotated in relation to the lead from the proximal end by means of the inner coil, which is rotatably arranged inside the lead. A rotatable helix can be rotatable but non-extendable in relation to the lead, or it can be rotatable and extendable, in which case the helix is accommodated inside a sleeve formed header in the distal end of the lead and will be screwed out from the header when attaching it to the tissue. In the latter case the inner coil will accordingly be stretched out when attaching the helix to the tissue. The penetration member can also function as an electrode inside the tissue, in which case the penetration member is electrically connected to the inner coil, or be separated from the electrode, in which case the penetration member is not electrically connected to the inner coil.

In the proximal end the inner coil is connected, mechanically as well as electrically, to a connector pin, which can be electrically connected to a monitoring and/or controlling device and which is accommodated in a connector housing. In case the lead comprises a rotatable helix in the distal end, the connector pin is rotatably journaled inside the connector housing.

As is evident from the above description, the inner coil will have several functions. Firstly, it will function as an electrical conductor for transferring of electrical signals between the monitoring and/or controlling device and the electrode in the distal end. In case the lead comprises a rotatable helix in the distal end, the inner coil shall also transfer rotary motion from the proximal to the distal end. In case the rotatable helix also is extendable, the inner coil will also be elongated to maintain the mechanical as well as electrical contact with the helix during rotation and advancement. Furthermore, the inner coil shall contribute to the desired bending characteristics of the lead, i.e. the lead has to be flexible but should have sufficient stiffness to be insertable through a vein or the like. Finally, the inner coil will define an inner lumen in the lead, into which a guide wire or stylet may be inserted during implantation, for guiding the distal end of the lead to a suitably position abutting with its distal end against an organ inside the body and subsequent fixation by the fixation means, e.g. by screwing in of the helix into the organ.

In the prior art, the inner wire coil is attached to the connector pin at a distal end portion of the connector pin. For example can the inner coil be welded to the connector pin or be attached by means of a clamp connection, in which case a proximal portion of the inner wire coil often is thread onto a support tube to prevent collapsing of the coil section during clamping, and the support tube as well as the thread up portion of the inner coil is inserted into a bore from the distal end of the connector pin and fixated therein by clamping and deforming of the connector pin. Accordingly, the connector pin in prior art is normally provided with an enlarged bore in a distal portion to allow insertion and attachment of the inner coil inside the connector pin. A proximal portion of the connector pin, on the other hand, is only provided with a small diameter bore to allow insertion of a guide wire or the like when implanting the lead into the body.

However, there are several disadvantages associated with attaching the inner coil with the connector pin in the distal end. For one thing, this operation is complex to perform since the available space to perform the attachment is very limited. Moreover, the inner coil has to be pre-cut in correct length before assembling, wherein the length cannot be altered afterwards, and this is critical since e.g. the performance of a rotatable and extendable fixation helix depends in high degree on the length of the inner coil. This is due to the fact that the inner coil in practice functions as a helical spring and tensile stress will arise in the inner coil if the length is to short, since then it has to be stretched when attaching to the connector pin, with the potential risk that the helix will tend to rotate after attaching to the organ which can cause disengagement of the lead from the organ. When such an incorrect length of the inner coil is detected after assembling but before use, the entire lead has to be discarded. Moreover, when the inner coil is attached to the connector pin, this can cause the coil windings to become uneven and wave shaped, which will increase the friction against an inner tubing, which encloses the inner coil and in relation to which the inner coil is rotatable. A medical implantable lead constructed in this way also has to be assembled by one component at a time from one of the ends of the lead. This has to effect that if one of all the components forming the medical implantable lead should fail or be incorrect mounted, the entire medical implantable lead has to be discarded.

The aggregate dimensional tolerances of the component parts as well as the assembling tolerances will affect the actual required length of the inner coil and hence it is difficult to estimate the nominal cut length of the inner coil in advance. This necessitates close dimensional as well as assembling tolerances, in order to limit the number of discards, and this increases the manufacturing costs for the medical implantable lead.

SUMMARY OF THE INVENTION

An object of the invention is to provide a medical implantable lead, which is possible to manufacture at a low cost, high quality and with improved helix performance.

The invention also relates to a method having essentially the same object as above.

Accordingly, the basis of the invention is the recognition that this object can be achieved by letting the inner coil extend through the entire connector pin and to attach the inner coil at the proximal end of the connector pin. In this way several advantages may be achieved. Since the inner coil is attached to the outer proximal end of the connector pin, the length of the inner coil can be cut as one of the last operations of the assembling of the medical implantable lead. Accordingly, the cut length of the inner coil can be adapted to the actual length due to the aggregate tolerances of the rest of the lead, such that the inner coil can be cut in a length that will not give any disadvantageous inherent tensions in the inner coil. As a result of this, the dimensional as well as the assembling tolerances can be allowed to increase with a lower cost for components and assembling. Also, any uneven windings of the inner coil caused by the attachment to the connector pin, will be disposed inside the inner bore of the connector pin and, accordingly, can not cause any seizing in relation to the inner tubing of the lead in case of a rotatable inner coil. Moreover, the initial length of the inner coil can be made in one size fitting all different lengths of medical implantable leads, which will reduce the number of pre-cutting fixtures. When the cutting of the inner coil is performed as one of the last operations, the possibility of getting rests of cut filaments inside the lead is reduced. It is also an advantage that the attachment of the inner coil to the connector pin will always be visible from the outside such that e.g. a weld connection can be easily verified.

Within the general inventive idea the invention may be modified in many different ways. For example, the inner coil can be directly attached to the proximal end of the connector pin, e.g. by welding. However, in a hereinafter described and illustrated embodiment of the invention, the inner coil is attached to the connector pin via a coil adapter having a shaft portion with a through lumen, onto which a few of the most proximal windings of the inner coil are thread and subsequently the coil adapter with the coil windings is inserted into a recess in the proximal end of the connector pin and attached, while a head of the coil adapter will remain on the outside of or flush with the proximal end of the connector pin. The attachment between the inner coil and the coil adapter as well as between the coil adapter and the connector pin, can be performed in many different ways, such as by welding, by laser or otherwise, soldering, crimp connection or adhesive bonding.

It is also conceivable to lock the coil adapter mechanically to the connector pin, e.g. by forming the proximal portion of the bore through the connector pin as well as the shaft of the coil adapter with a conical shape, which will engage firmly when compressed.

According to an embodiment of the invention, it is possible to assemble the medical implantable lead into two different sub-assemblies, more precisely a first sub-assembly comprising the inner coil and a distal header comprising a fixation means, and a second sub-assembly comprising a casing defined by an outer tubing, an outer coil, optional a ring electrode, an inner tubing and a connector comprising the connector pin in a proximal end. Firstly the outer tubing, the outer coil and the inner tubing of the second sub-assembly are cut to the correct length. Thereafter the free end of the inner coil of the first sub-assembly is inserted into the inner lumen defined by the outer tubing, the outer coil and the inner tubing of the second sub-assembly, until the inner coil projects from the proximal end of the connector pin and the distal ends of the outer tubing, outer coil and inner tubing abuts the proximal end of the header. Subsequently, the inner tubing, the outer coil and the outer tubing are attached in correct position to the header. At this stage the length of the lead is fixed. The only thing remaining is to cut the inner coil in length and attach the inner coil to the proximal end of the connector pin.

BRIEF DESCRIPTION OF THE DRAWINGS

FIG. 2 is a longitudinal section through a header having a helix in a retracted state.

FIG. 3 is a section according to FIG. 2, with the helix in an extended state.

FIG. 4 is a longitudinal section through a connector according to the invention, into which an inner coil is being inserted.

FIG. 5 is a section according to FIG. 4, with the inner coil fully inserted and cut.

FIG. 6 is a longitudinal section through the connector according to FIGS. 4 and 5, with the inner coil attached.

DESCRIPTION OF THE PREFERRED EMBODIMENTS

Figure 1:
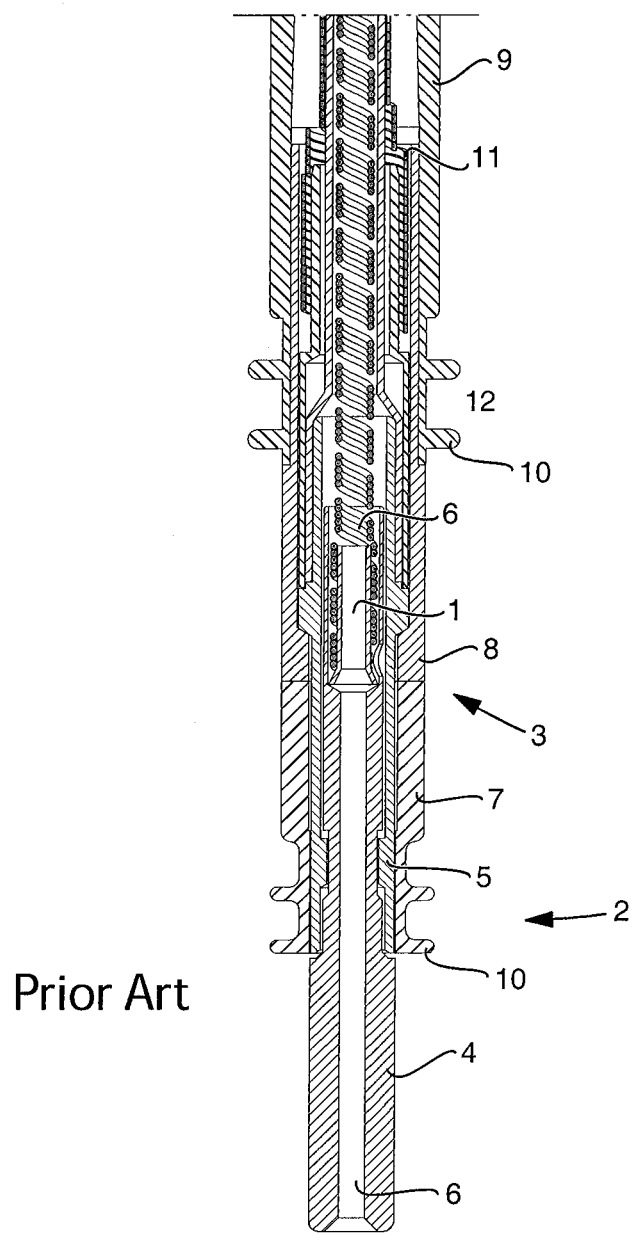
FIG. 1 is a longitudinal section through a prior art connector illustrating the attachment of the inner coil to the connection pin.

Reference is first made to FIG. 1 in which is illustrated, in a longitudinal section, a prior art embodiment of a proximal portion of a medical implantable lead. In the proximal end the lead is provided with a connector 2 for mechanical as well as electrical connection of the lead to a monitoring and/or controlling device, such as a pacemaker or a cardiac defibrillator. The connector 2 has a connector housing 3 in which a connector pin 4 is rotatably accommodated by being rotatable mounted in a bearing sleeve 5 inside the connector housing 3. The connector pin 4 is electrically conductive and is in its distal end connected, mechanically as well as electrically, to an inner coil 6 of helically wound metallic wires, e.g. by a clamp connection. More precisely, the inner coil 6 is thread onto a support tube 1, which is inserted into a bore having an enlarged diameter in the distal portion of the connector pin 4. Subsequently, the distal portion of the connector pin is deformed by clamping such that the inner coil 6 is clamped between the connector pin 4 and the support tube 1. Where the enlarged diameter bore terminates, the bore transforms to a small diameter lumen adapted only for insertion of a guide wire or the like, when implanting the lead. The connector housing 3 is assembled of a proximal sealing member 7, an intermediate connector ring 8 and a distal sealing member 9. Both of the sealing members 7 and 9 are of an electrically insulating material and are provided with resilient sealing flanges 10 for allowing fluid tight connection to the monitoring and/or controlling device. The connector ring 8 is electrically conductive and is connected to an outer coil 11 of helically wound metallic wires. An inner tubing 12 is positioned between the inner coil 6 and the outer coil 11 for electrical insulation of the inner and outer coils in relation to each other. The inner coil 6 is also rotatable with respect to the inner tubing 12. With a medical implantable lead constructed in this way it is possible to connect a first electrical terminal in the monitoring and/or controlling device to the connector pin 4 to utilize a helix as an electrode in the tissue of the heart, whereas a second electrical terminal of the monitoring and/or controlling device is connected to the connector ring 8 and is by means of the outer coil 11 connected to a second electrode, e.g. a ring electrode on the outside of the distal end of the medical implantable lead. However, the attachment between the inner coil 6 and the connector pin 4 is difficult to accomplish since it has to be made when the rest of the lead, except for the connector housing 3 already is assembled, such that very little space is available to perform the attachment. Moreover, when attaching the inner coil 6 to the connector pin 4, it often happens that the windings of the inner coil will become uneven and wave formed, which might cause friction between the inner coil and the inner tubing 12.

The present detailed description describes a medical implantable lead, according to the invention as well as according to a prior art embodiment, which is of the type provided with a rotatable as well as extendable helix in the distal end for attachment to a heart by being screwed into the tissue of the heart. This is illustrated in FIGS. 2 and 3, which are longitudinal sections of a distal portion of a medical implantable lead comprising a sleeve formed header 13 in the distal end. When the lead is inserted into or withdrawn from a body, a helix 14 is accommodated inside the sleeve formed header, as is illustrated in FIG. 2. When the lead is correct positioned inside the body with its distal end abutting against an organ, the lead can be attached to the tissue by rotation of the inner coil 6, wherein the helix 14 will be screwed out from the header 13 and into the tissue, as is illustrated in FIG. 3. Accordingly, the inner coil 6 will be slightly stretched out when extending the helix from the header. Visible in FIGS. 2 and 3 are also the inner tubing 12, the outer coil 11 and an outer tubing 15 and their respective attachment to the header 13. The outer coil 11 is electrically connected to a ring electrode 16 on the outside of the header.

Now reference is made to the longitudinal sections of FIGS. 4-6, of a proximal connector portion of a medical implantable lead according to an embodiment of the present invention. The overall structure of this medical implantable lead corresponds essentially to the lead in FIG. 1 of the prior art embodiment. Accordingly, the connector 2 comprises a connector housing 3 in which a connector pin 4 is rotatably accommodated by being rotatably mounted in a bearing sleeve 5. An inner coil 6 is mechanically and electrically connected to the connector pin 4. The connector housing 3 comprises a proximal sealing member 7, an intermediate connector ring 8 and a distal sealing member 9. Both the sealing members 7 and 9 is provided with sealing flanges 10. The connector ring 8 is connected to an outer coil 11 and an inner tubing 12 is arranged between the inner coil 6 and the outer coil 11 to insulate them electrically from each other. The inner tubing also allows rotation of the inner coil 6. In the distal end of the connector 2, an outer tubing is attached.

However, according to the invention, the attachment of the inner coil 6 to the connector pin 4, is in FIGS. 4-6 performed in a different way in relation to the prior art embodiment in FIG. 1. More precisely, instead of attaching the inner coil to the distal end of the connector pin, as in FIG. 1, the connector pin is provided with an enlarged inner bore 17, such that the inner coil can be passed through the entire connector pin and attached in the proximal end of the same.

A procedure for attaching the inner coil to the connector pin is illustrated in FIGS. 4-6. When inserting the inner coil into the inner lumen of the inner tubing 12, the connector 2 can preferably be assembled and connected to the inner tubing 12, the outer coil 11 and the outer tubing 15, as is illustrated in FIG. 4. To assist in introducing the inner coil 6 through the inner tubing 12, a guide wire 18 can preferably be inserted in the inner lumen of the inner coil 6 for stiffening of the latter.

When the inner coil 6 is fully inserted such that an end of the inner coil projects from the proximal end of the connector 2, the inner coil can be cut to a desired length, as is illustrated in FIG. 5. Subsequently, the proximal end of the inner coil is thread up on a coil adapter 19, as is illustrated in FIGS. 5 and 6. The coil adapter is provided with an inner lumen 20, a shaft portion 21 and a head portion 22. When mounting the inner coil, a few of the most proximal windings are thread up on the shaft portion 21 and fixated by means of e.g. laser welding. Thereafter the coil adapter together with the inner coil is inserted into the inner bore 17 of the connector pin 4 which is formed with an enlarged portion in the proximal end to accommodate the shaft portion as well as the head portion of the coil adapter, such that the coil adapter will be positioned with its head portion flush with the proximal end of the connector pin. To eliminate any tensile stress in the inner coil, it is advantageous to compress the inner coil slightly when mounting it in the connector pin. This can easily be done by having the inner coil relaxed in the cut stage in FIG. 4, when the inner coil is slightly longer than the rest of the lead, and then push the inner coil together with the coil adapter into the bore 17 of the connector pin, as is illustrated in FIG. 5.

Figure 7:
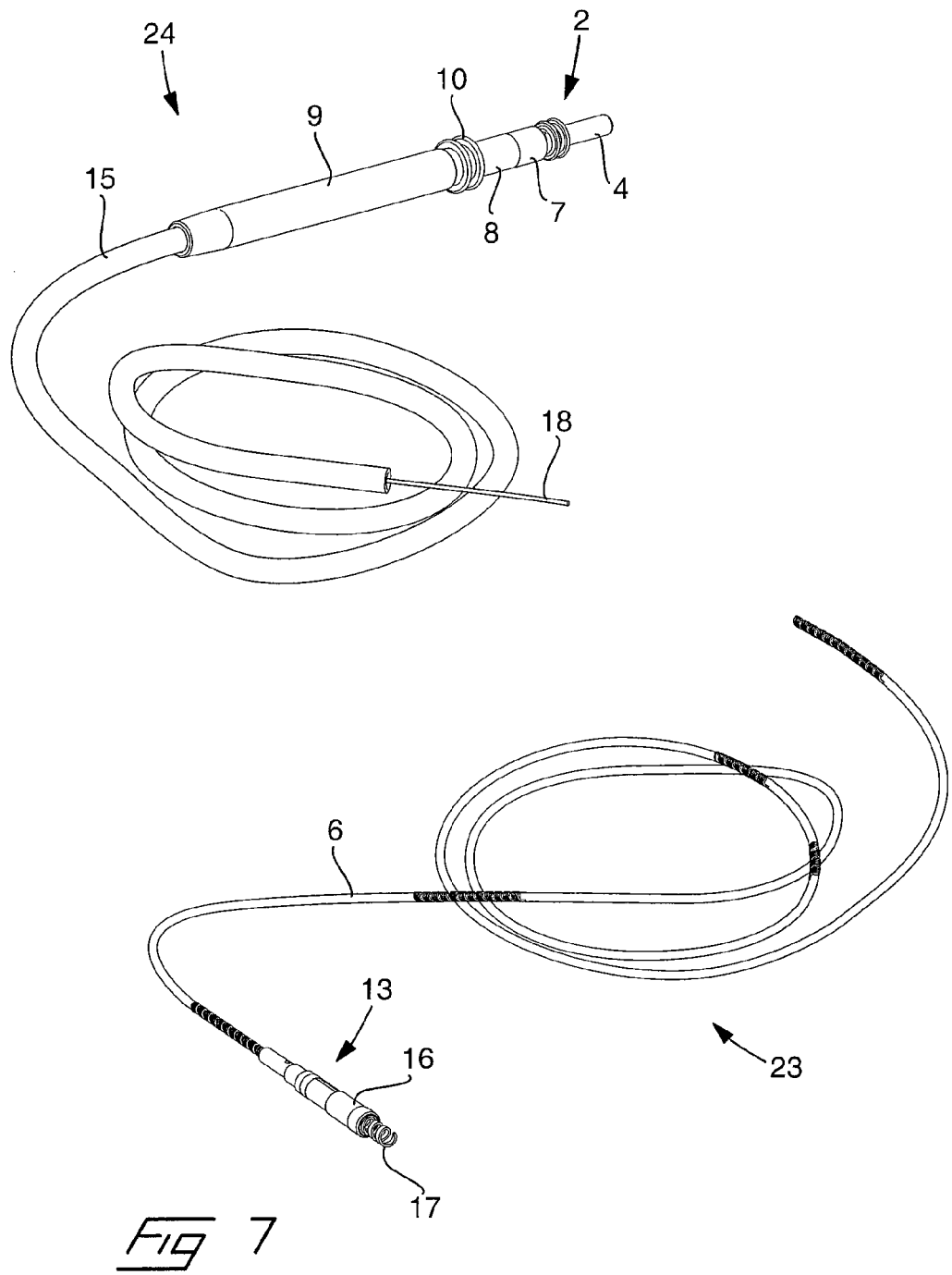
FIG. 7 is a view illustrating the assembling of the medical implantable lead from two sub-assemblies.

By designing a medical implantable lead according to the invention, a new method for assembling the lead is made possible. More precisely, it is made possible to construct the lead as two separate sub-assemblies, which are combined as a last assembly step. This is illustrated in FIG. 7, where a first sub-assembly 23 comprises the header 13, including the helix, and the inner coil 6 attached to the header. A second sub-assembly 24 is comprised of the connector 2 and an outer casing formed by the inner tubing 12, the outer coil 11 and the outer tubing 15. Before assembling, the respective sub-assembly may preferably be tested visually and functionally. Thereafter, the proximal end of the inner coil 6 is inserted into the distal end of the lumen constituted by the inner tubing 12, the outer coil 11 and the outer tubing 15, such that the proximal end of the inner coil 6 projects from the proximal end of the connector 2, as is illustrated in FIG. 4. To facilitate inserting of the inner coil into the casing of the second sub-assembly, preferably a guide wire 18 can be utilized to stiffen the inner coil. Subsequently, the respective layer constituted by the inner tubing 12, the outer coil 11 and the outer tubing 15 are attached to the proximal end of the header 13 of the first sub-assembly. When that is done the length of the lead is fixed and accordingly, the proximal end of the inner coil can be cut, as illustrated in FIG. 5, and attached to the connector 2, as illustrated in FIG. 6.

Although modifications and changes may be suggested by those skilled in the art, it is the intention of the inventors to embody within the patent warranted heron all changes and modifications as reasonably and properly come within the scope of their contribution to the art.

What is claimed is:

1. A method to manufacture an implantable medical lead having a lead body with a distal end, a proximal end, and a hollow interior proceeding between the distal end and the proximal end, the method comprising:

manufacturing a connector pin with a configuration to mechanically and electrically attach the proximal end of the lead body to an electronic device, and with an inner bore proceeding through the connector pin;

attaching the connector pin to the proximal end of the lead body;

introducing an inner coil from the distal end of the lead body through the inner bore of the connector pin, and leaving the inner coil so that the inner coil protrudes a distance beyond a proximal end of the connector pin;

the method further comprising:

forming a first sub-assembly by attaching a header, containing a fixation arrangement to the inner coil;

assembling a second sub-assembly comprising an outer casing of the lead body and a connector;

assembling the first and second sub-assemblies by introducing the proximal end of the inner coil into a distal end of the outer casing to cause the proximal end of the inner coil to project from the proximal end of the connector pin;

cutting the inner coil to a selected length at the proximal end of the connector pin; and attaching the proximal end of the inner coil to the proximal end of the connector pin.

2. The method as claimed in claim 1, further comprising attaching the inner coil to the connector pin by attaching the inner coil to a coil adapter and attaching the coil adapter to the proximal end of the connector pin.

3. The method as claimed in claim 1, further comprising mounting a rotatable helix to a distal end of the inner coil.

4. A method to manufacture an implantable medical lead having a lead body with a proximal end, a distal end, and a hollow interior proceeding between the proximal end and the distal end, the method comprising:

disposing a header at the distal end of the lead body;

disposing a fixation arrangement and an electrode in the header, the fixation arrangement being adapted to attach the distal end of the lead body to an organ in vivo and the electrode being adapted to transmit or receive electrical signals to or from the organ;

disposing a connector at the proximal end of the lead body, the connector having a connector housing and a connector pin, the connector pin located within the connector housing, and the connector being configured for mechanical and electrical connection to an electronic device;

extending an inner coil along a length of the lead body inside the hollow interior casing and transmitting electrical signals between the connector pin and the electrode;

extending the inner coil through a bore of the connector pin; and securing a coil adapter within the bore at a proximal portion of the connector pin, the coil adapter having an inner lumen, a shaft portion at a distal portion of the coil adapter, and a head portion at a proximal portion of the coil adapter, the shaft portion configured to receive and secure a proximal end of the inner coil so at to secure the proximal end of the inner coil to the proximal portion of the connector pin.

5. The method as claimed in claim 4, wherein the fixation arrangement comprises a rotatable helix that is rotatable by the inner coil and the connector.

\* \* \* \* \*